United States Patent [19]

Morris et al.

[11] Patent Number: 5,068,362
[45] Date of Patent: Nov. 26, 1991

[54] CYCLIC ETHERS AND THEIR UTILIZATION AS PERFUMING OR FLAVORING INGREDIENTS

[75] Inventors: Anthony F. Morris, Gingins; Regula Naef, Carouge; Sina Escher, Confignon, all of Switzerland; Alain Velluz, La Roche/Foron, France

[73] Assignee: Firmenich SA, Geneva, Switzerland

[21] Appl. No.: 623,146

[22] Filed: Dec. 5, 1990

Related U.S. Application Data

[62] Division of Ser. No. 439,406, Nov. 21, 1989, Pat. No. 5,021,402.

[30] Foreign Application Priority Data

Nov. 28, 1988 [CH] Switzerland ............... 4414/88

[51] Int. Cl.⁵ .......................................... C07D 325/00
[52] U.S. Cl. ................................................. 549/346
[58] Field of Search ......................................... 549/346

[56] References Cited

U.S. PATENT DOCUMENTS 3,163,658 12/1964 Eschinasia et al. ............... 549/346
3,328,426 6/1967 Oholoff et al. ...................... 549/346

OTHER PUBLICATIONS

Shono, T. "Pyrans and Thiopyrans," *Chemical Abstracts* 1972, vol. 77 at 424.

*Primary Examiner*—James H. Reamer
*Attorney, Agent, or Firm*—Pennie & Edmonds

[57] ABSTRACT

Cyclic ethers of formula

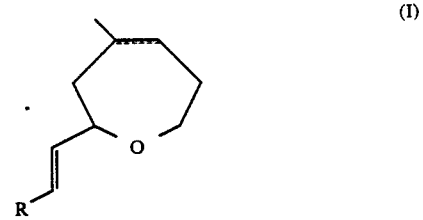

(I)

wherein the dotted line indicates the location of a single or double bond and the symbol R represents an isopropenyl radical or a 1-ethoxy-1-methylethyl radical, are novel compounds with useful organoleptic properties. They can be used as active ingredients in perfuming compositions and perfumed products to which they confer rosy-fruity type odor notes. In addition, they possess flavor qualities which render these compounds useful for flavoring foodstuffs and drinks and, namely, mango-type drinks.

A process for the preparation of the compounds of formula (I) is also disclosed.

5 Claims, No Drawings

CYCLIC ETHERS AND THEIR UTILIZATION AS PERFUMING OR FLAVORING INGREDIENTS

This is a division of application Ser. No. 07/439,406, filed Nov. 21, 1989, U.S. Pat. No. 5,021,402.

BRIEF SUMMARY OF THE INVENTION

The present invention relates to the fragrance and flavor industries. It concerns more particularly a novel compound of formula

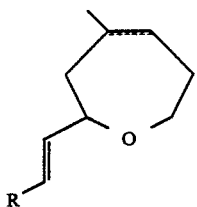

(I)

wherein the dotted line indicates the location of a single or double bond and the symbol R stands for an isopropenyl radical or a 1-ethoxy-1-methylethyl radical.

The invention also provides a method to confer, enhance, improve or modify the organoleptic properties of a perfuming or flavoring composition, or a perfumed or flavored product, which method comprises adding to said composition or product an organoleptically effective amount of a compound of formula (I) as defined.

Another object of the invention is a perfuming composition or a perfumed product containing as an active ingredient a compound of formula (I) as defined above.

Yet another object of the invention is a flavoring composition or a flavored product containing a compound (I) as an active ingredient.

The invention further provides a process for the preparation of a compound of formula (I) as defined above, which process comprises reacting a compound of formula

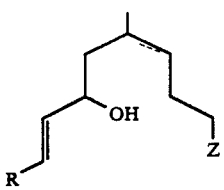

(III)

wherein the dotted line indicates the location of a single or double bond, the symbol Z represents a leaving group under the reaction conditions and the symbol R is defined as in formula (I), with a strong base, in the presence of an inert organic solvent.

THE INVENTION

We have now discovered unexpectedly that the ethers of formula (I) defined above possess very useful odor properties. In fact, they develop floral, slightly fruity, even metallic odor notes.

The ethers of formula (I) are natural occurring compounds. We have in fact discovered that these compounds can be found in infinitesimal quantities, of the order of 50 ppm (parts per million) in the quince fruits (Cydonia oblonga Mill.) and/or in the brandy obtained by distillation of the fermented quince juice.

The extraction of compounds (I) was achieved by means of a complex method of codistillation in an apparatus of the type known as Likens-Nickerson, starting from fresh quince fruits, followed by a chromatographic separation on a silica gel column, using a pentane/diethylether (9:1) mixture as the elution agent. The identification of each compound was then carried out through various spectroscopic methods, among which one can cite mass spectrometry and nuclear magnetic resonance.

On the other hand, the isolation of these compounds from the quince brandy was carried out by means of extraction in a device known as the Kutscher-Steudel apparatus.

The following description gives the details of the practiced methods.

a. Codistillation 1.4 kg of fresh fruit, previously cut in the shape of small cubes, were ground in 2.250 l of water in a mixer and subjected to distillation in a Likens-Nickerson apparatus [see Proc. Am. Soc. Brew. Chem. 5, (1964)]. This is actually an apparatus which has been modified according to the instructions disclosed in J. Agr. Food Chem. 25, 1946 (1977) by T. Schultz et al. The distillation occurred in the presence of 150 ml of pentane and took 5 hours to be completed. The extracts thus obtained were dried on magnesium sulfate, then concentrated in a distillation apparatus equipped with a Vigreux type column. The product thus obtained as a residue was fractionated by chromatography on a column filled with silica gel and using as elution agent a mixture of pentane and diethyl ether (9:1). In this way, 2,3,6,7-tetrahydro-4-methyl-2-(3-methyl-1,3-butadienyl)oxepin, or 4-methyl-2-(3-methyl-1,3-butadienyl)-1-oxa-4-cycloheptene, was isolated in the apolar fraction. The gas chromatography analysis showed that the retention times were 26′40″ on a CARBOWAX column [Supelco®, 60 m/0.25 mm; 80°–250° C.; $\Delta T = 5°/min$; flow: 1.2 kg He] and 18′50″ on an apolar SPB column [Supelco®, 60 m/0.25 mm; 80°–250° C.; $\Delta T = 5°/min$; flow: 1.5 kg He].

Analytical data for 2,3,6,7-tetrahydro-4-methyl-2-(3-methyl-1,3-butadienyl)oxepin thus obtained:

MS: 178($M^+$,2); m/z: 163(4), 135(5), 110(4), 96(7), 82(35), 67(100), 53(8), 41(7)

$^1$H-NMR(360 MHz): 1.77(3H,s); 2.10(1 H,d,J=16 Hz); 2.18(1 H,m); 2.40(1H,dxd,$J_1$=9Hz,$J_2$=16Hz); 2,55(1H,dxd,$J_1$=16 Hz,$J_2$=11Hz); 3.55(1H,dxd,$J_1$=9Hz, $J_2$=12Hz); 4.05(2H,m); 4.98(2H,m); 5.60(1H,m); 5.70(1H,dxd,$J_1$=16Hz, $J_2$=7Hz); 6.33(1H,d,J=16Hz) δ ppm.

b. Kutscher-Steudel extraction 4,9 liters of quince brandy [commercial product; origin: "Coing du Feuillu", Saconnex-d'Arve, Geneva, reserve (1982)] were diluted in 4 l of water and continuously extracted with 1 l of diethyl ether for 20 hours in a Kutscher-Steudel apparatus [see: Hoppe-Seyler's Z. physiolog. Chem. 39, 473 (1903)]. The ethereal solution was then concentrated in a distillation apparatus provided with a Vigreux column and the procedure was repeated once again on a fresh 5 l amount of brandy.

The residues obtained from the two extractions (25.5 g), containing mainly ethanol, were fractionated by distillation under vacuum at 7.98–5.32 Pa. At this pressure, the alcohol was eliminated at 24°–25° C. and 1.05 g of an extract were obtained, which were subjected to column chromatography separation and fractioning following the method indicated under a. above.

The 2,3,6,7-tetrahydro-4-methyl-2-(3-methyl-1,3-butadienyl)oxepin obtained in this extraction was in every way identical to the product obtained and described in a. above.

Other compounds were also separated and their chemical structures established on the basis of the analytical data, as follows:

4-methyl-2-(3-methyl-1,3-butadienyl)oxepane or 4-methyl-2-(3-methyl-1,3-butadienyl)-1-oxa-cycloheptane Two isomers were identified as follows:
Isomer A:
Retention time on a CARBOWAX column [conditions defined in a.]: 24'25"
MS: 180(M+,40); m/z: 165(82), 151(6), 137(17), 123(12), 111(43), 96(53), 81(52), 69(100), 55(96), 41(87).
Isomer B:
Retention time on a CARBOWAX column [conditions defined in a.]: 25'00"
MS: 180(M+,41); m/z: 165(90), 151(6), 137(17), 123(12), 111(45), 96(62), 81(73), 69(100), 55(72), 41(95).

2-(3-ethoxy-3-methyl-1-butenyl)-2,3,6,7-tetrahydro-4-methyloxepin or 2-(3-ethoxy-3-methyl-1-butenyl)-1-oxa-4-cycloheptene Retention time on a CARBOWAX column [conditions defined in a.]: 26'35"
MS: 224(M+,0,5); m/z: 209(4), 178(14), 163(6), 155(8), 142(5), 135(7), 113(13), 97(8), 87(18), 82(54), 67(100), 43(28).

The chemical structures established for these natural compounds on the basis of their above-mentioned analytical data are defined by means of formula (I) cited and have been confirmed by synthetical preparation as described further on. Their's is in fact a quite uncommon type of structure and, up until now, unknown for naturally occurring fragrant compounds.

According to the invention, the compounds of formula (I) can be used as active ingredients in perfuming compositions, perfumes or perfumed products. The latter may be quite varied, for instance, soaps, liquid or solid, cationic or zwitterionic detergents, fabric softeners, household products, body or room deodorants. Other such perfumed products include shampoos, cosmetic preparations or hair products.

The cyclic ethers (I) according to the invention also find particular use in the reconstitution of essential oils, namely of the floral type.

The compounds of formula (I) possess significantly different odor properties from one compound to the next, in spite of their very slight structural variations. Thus, the odor of 2,3,6,7-tetrahydro-4-methyl-2-(3-methyl-1,3-butadienyl)oxepin, a preferred compound according to the invention, can be defined as floral, rosy. Certain odor characters of this unsaturated cyclic ether are reminiscent of the fragrance of rose oxide, but its odor note is in fact richer, fuller and sweeter than that of rose oxide. It is also a powerful and highly diffusive odor note.

Another preferred compound of the invention, 4-methyl-2-(3-methyl-1,3-butadienyl)oxepane (isomer mixture), develops a floral type odor note, rose green, rose oxide, less fruity, powerful and characteristic than that of its above-mentioned unsaturated analog. The synthesis of this oxepane made it possible to evaluate separately the two isomers A and B cited before and represented by the formula

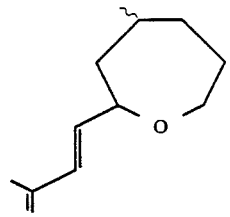

(II)

wherein the wavy line defines a C—C bond of cis or trans configuration. It was then found that isomer A developed an odor note of the green, floral type, with a pleasant bitter character reminiscent of hyacinth, also fatty and fruity, whilst isomer B had a green, metallic odor, more powerful than that of isomer A.

As for 2-(3-ethoxy-3-methyl-1-butenyl)-2,3,6,7-tetrahydro-4-methyloxepin, it possesses a floral, green, rose, hyacinth fragrant note, with a leafy bitter green character.

When acting as perfuming ingredients, the compounds of formula (I) can be used in proportions varying in a wide range of values. The man in the art knows by experience that such values are a function of the fragrance effect desired, of the nature of the other coingredients in a given composition and, naturally, of the nature of the product to be perfumed.

As regards flavor properties, one finds yet again that each of the above-mentioned compounds has specific qualities. For example, 2,3,6,7-tetrahydro-4-methyl-2-(3-methyl-1,3-butadienyl)oxepin has a woody, green, geranium type flavor note, with a nuance in the direction of rose oxide, also fruity, mango-type, while its saturated analog or 4-methyl-2-(3-methyl-1,3-butadienyl)oxepane is characterized by a rosy, fatty and green flavor note, slightly dirty, metallic and fermented, with a tropical fruit nuance.

The proportions in which the compounds (I) can be used as flavor ingredients can likewise vary in a wide range of values. However, they will be considerably lower than the proportions used for the above-mentioned perfumery applications. Amongst the products that can be flavored with the compounds of the invention, one can obviously mention foodstuffs and drinks. Nevertheless, the compounds of formula (I) can be employed with equal advantage to confer, enhance, improve or modify the flavor and taste of varied products such as tobacco, spices or chewing-gum.

The compounds according to the invention can be prepared following a process with is a further object of the present invention. This process comprises reacting a compound of formula

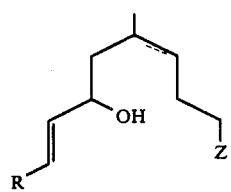

(III)

wherein the dotted line indicates the location of a single or double bond, the symbol Z represents a leaving group under the reaction conditions and the symbol R is defined as in formula (I), with a strong base, in the presence of an inert organic solvent.

The reaction which characterizes the process according to the invention is in fact a cyclisation or an intramolecular etherification obtained by means of a strong base and in the presence of an inert organic solvent capable of stabilizing the alcoholate formed in said reaction. As the strong base in this process, one can use a mineral or organic base such as an alkali metal hydride or alkoxide, preferably a sodium or potassium hydride or alkoxide. Amongst the said bases, one can cite sodium or potassium hydride and sodium or potassium tert-butylate.

As previously cited, the reaction can take place in an inert organic solvent. To this effect, organic solvents such as ethers, for example, tetrahydrofurane (THF) or ethyleneglycol dimethylether (monoglyme), in admixture with amides such as hexamethylphosphoric triamide (HMPT) or yet N,N'-dimethyl-N,N'-propylene urea [(DMPU); see T. Mukhopadhyary and D. Seebach, Helv. Chim. Acta 65, 385 (1982)], can be used.

According to a preferred embodiment of the process of the invention, sodium hydride is used as a strong base and the reaction takes place in a mixture of monoglyme and DMPU.

In formula (III) previously defined, symbol Z stands for a leaving group under the conditions of the above-described reaction, for instance it stands for a p-toluenesulfonyloxy radical.

The compounds of the invention for which symbol R in formula (I) represents a 1-ethoxy-1-methylethyl radical can also be prepared starting from compounds (I) for which symbol R stands for an isopropenyl radical by reacting the latter with ethanol in the presence of p-toluenesulfonic acid.

The compounds of formula (III) defined above, used as starting products in the process according to the invention, can be obtained by means of a multi-step method represented by the following scheme:

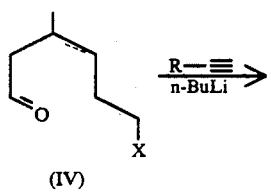

(IV)

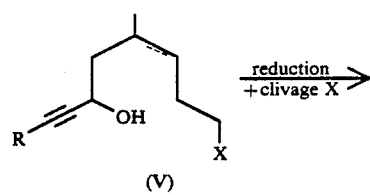

(V)

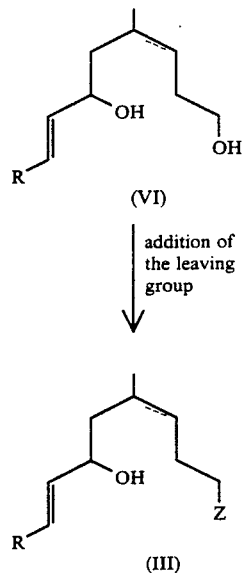

In this scheme, the dotted line indicates everywhere the location of a single or double bond, symbol R in formulae (III), (V) and (VI) represents an isopropenyl radical or a 1-ethoxy-1-methylethyl radical, symbol X in formulae (IV) and (V) represents a protecting group under the conditions of the indicated reactions, for example an acetyloxy or tetrahydro-2(2H)-pyranyloxy radical and symbol Z in formula (III) is defined as before.

Aldehydes (IV) are novel compounds which can be prepared by classical type reactions from known products as it is described in the preparation examples presented further on. The reaction of these aldehydes with the lithium salt of the alkynyl cited above, under known conditions (see for example L. Brandsma in "Preparative Acetylenic Chemistry", Elsevier, Amsterdam, 2nd ed., 1988, page 82), gives the enynol (V) in quantitative yield. The following step of the process represented above comprises the reduction of this enynol, for instance by means of $LiAlH_4$, which, depending on the nature of the protecting group X, may be accompanied by the simultaneous clivage of this latter group or, if required, is followed by an hydrolysis to give diol (VI). The latter is then converted into the desired product (III) in a classical way, for example using p-toluenesulfonyl chloride, in pyridine.

The specific conditions in which the reactions illustrated in the scheme presented above took place will be described in detail in the preparation examples presented hereinafter, wherein the temperatures are indicated in degrees Celsius and the abbreviations have the usual meaning in the art.

The present invention will also be described in greater detail by way of the application examples presented further on.

EXAMPLE 1

Preparation of (E)-2,3,6,7-tetrahydro-4-methyl-2-(3-methyl-1,3-butadienyl)oxepin a)
(Z)-2-methyl-5-(tetrahydro-2(2H)-pyranyloxy)-2-penten-1-ol

A procedure analogous to that described by M. Schlosser et al. in Synthesis 1971, 380 and E. J. Corey et al. in J. Amer. Chem. Soc 92, 226 (1970) was followed. A four necked flask equipped with a mechanical stirrer, a refrigerator, an argon inlet, an introduction funnel and a thermometer was charged with 55.6 g (150 mmole) of ethyltriphenylphosphonium bromide and 300 ml of anhydrous THF (freshly distilled from LiAlH$_4$) and cooled in an ice-water bath. A solution of n-butyllithium in hexane (1.44 M, 104 ml, 150 mmole) was introduced dropwise producing a deep red solution which, after being stirred for 1 hour at room temperature, was cooled to $-70°$. 23.7 g (150 mmole) of 3-(tetrahydro-2(2H)-pyranyloxy)propanol [obtained according to the process described, for example, by W. Kitchlin et al. in J. Org. Chem. 54, 3893 (1989)] in THF (71ml) were added to the mixture over 20 min while the internal temperature remained below $-60°$. The intense color faded. After stirring for 20 min at $-70°$, a second equivalent of n-butyllithium in hexane was introduced over 20 min. The now black solution was then warmed to $-5°$ and a solution of formaldehyde in THF (ca. 0.7 M, 450 ml, ca. 315 mmole; prepared immediately before use at $-78°$ as described by M. Schlosser, ref. cited) was syphoned via a stainless steel capillary tube into the reaction flask. Decoloration of the reaction medium took place and a white precipitate was formed. Stirring was continued overnight at room temperature. 74 ml of water were then added and, after 2 hours, the orange solution was concentrated to 200 ml at reduced pressure, diluted with water (350 ml) and extracted with ether. The organic phase was washed to neutrality, dried over MgSO$_4$ and concentrated at reduced pressure. The crude product thus obtained was distilled on a 12 cm Vigreux column. The fractions distilling at $60°-90°/6.65 \times 10$ Pa yielded 20.3 g of about 80% pure alcohol. This material was combined with 22.1 g of a similar product obtained from a parallel run and redistilled in a 12 cm Vigreux column. 35.01 g of (Z)-2-methyl-5-(tetrahydro-2(2H)-pyranyloxy)-2-penten-1-ol 95% pure were thus obtained. B.p..85°-89°/6.65 $\times$ 10 Pa; yield. 58.3%.

An analytical sample of this compound was prepared by preparative gas chromatography and showed the following analytical data:

IR (liq.): 3400, 1205, 1140, 1125, 1080, 1040, 905, 880, 820 cm$^{-1}$;

NMR ($^1$H,360 MHz): 1.84(s,3H); 2.38(m,2H); 3.38, 3.51, 3.78, 3.84(4m,4H); 4.03, 4.09(AB,J=8.3Hz,1H); 4.61(m,1H); 5.35(t,J=9.0Hz,1H) δ ppm;

MS: 200(0,M+); m/z: 85(100), 43(20), 67(18), 57(17), 101(9), 116(2), 170(1).

b)
(Z)-1-bromo-2-methyl-5-(tetrahydro-2(2H)-pyranyloxy)-2-pentene

A solution of the alcohol prepared according to a) (8.00 g, 40 mmole) in hexane (400 ml) containing pyridine (4 ml) was treated dropwise, at $-7°$, with PBr$_3$ (4 ml, 42.4 mmole) in hexane (80 ml). When the introduction was completed (60 min), the mixture was stirred for another 30 min at $-5°$, then poured on an ice-water mixture and extracted with ether. The organic phase was then treated in the way previously described. 4.40 g of crude bromide were obtained and they were used without further purification in the next step.

NMR($^1$H,360 MHz): 1.85(s,3H); 2.38(m,2H); 3.44, 3.55, 3.76, 3.85(4m,4H); 4.00(s,2H); 4.60(m,1H); 5.44(t,J=7.6Hz,1H) δ ppm.

c)
(Z)-2-[2-methyl-5-(tetrahydro-2(2H)-pyranyloxy)-2-pentenyl]-1,3-dithiane

A solution of 1,3-dithiane (33 mmole) in anhydrous THF (33 ml, freshly distilled from LiAlH$_4$) was treated with a solution of n-butyllithium in hexane (1.45 M, 23 ml, 33.3 mmole) under argon at $-20°$. The mixture was stirred for 75 min at $-20°$ and then cooled to $-70°$. The bromide prepared according to b) (8.70 g, 33 mmole) in THF (11 ml) was added dropwise to the mixture such as to maintain the temperature below $-45°$. The reaction flask was disconnected from the argon inlet, stoppered and stored in the freezer ($-20°$) overnight. The mixture was then allowed to warm up to room temperature and washed with ether, the organic phase being subsequently treated in the usual way. The crude reaction mixture (12.8 g) was filtered through silica gel (100 g), using a mixture of hexane-ethyl acetate (8:2) as elution agent. 8.5 g of a product which, according to the chromatographic analysis, contained several other non identified compounds besides the desired dithiane, were obtained. This product, combined with 8.0 g of a similar compound obtained in a parallel run, was purified by medium pressure chromatography [MPLC, LOBAR ® column (origin: Merck), 85:15 mixture of hexane-ethyl acetate as elution agent]. 12.85 g of pure product were thus obtained (yield: 65.5%)

IR (liq.): 1200, 1180, 1140, 1120, 1080, 1040, 990, 970, 910, 880, 820 cm$^{-1}$;

NMR ($^1$H,360 MHz): 1.78(s,3H); 2.50(d,J=7.5 Hz,2H); 2.65(m,4H); 3.41, 3.50, 3.73, 3.87(4m,4H); 4.21(t,J=7.5 Hz,1H); 4.60(m,1H); 5.37(t,J=7.2 Hz,1H) δ ppm;

SM: 302(1,M+); m/z: 85(100), 119(53), 43(20), 67(15), 57(14).

d)
(Z)-3-methyl-6-(tetrahydro-2(2H)-pyranyloxy)-3-hexenal

A method analogous to that described by R. L. Markezich et al. in J. Amer. Chem. Soc. 95, 4414 (1973) and W. S. Johnson et al., ibid. 98, 1039 (1976) was followed for the preparation of this compound. To a mixture of the dithiane prepared according to c) (6.25 g, 20.7 mmole) and anhydrous powder of CaCO$_3$ (8.28 g, 82.8 mmole) in aqueous acetonitrile (1:4, 106 ml), maintained under argon and vigourously stirred, was added dropwise freshly distilled methyl iodide (12.4 ml, 199 mmole). The mixture was stirred overnight under argon and at room temperature, extracted with ether and the organic phase treated as usual. The crude product was bulb-to-bulb distilled at 130°-140°/6.65 $\times$ 10 Pa. 3.80 g (yield: 86.6%) of the desired aldehyde were obtained and used as such in the next step.

IR. 1715, 1210, 1140, 1130, 1080, 1040, 990, 910, 880, 820 cm$^{-1}$;

NMR ($^1$H,360 MHz): 1.78(s,3H); 3.12(m,2H); 3.40, 3.50, 3.75, 3.86(4m,4H); 4.58(m,1H); 5.52(t,J=7.2 Hz,1H); 9.60(t,J=1.8 Hz,1H) δ ppm;

MS: (0,M+); m/z: 85(100), 67(22), 55(17), 41(10), 101(11), 93(10), 110(4), 128(1), 183(1).

e)
(E)-2,7-dimethyl-10-(tetrahydro-2(2H)-pyranyloxy)-3-decyn-1,7-dien-5-ol Into an argon flushed solution of 2-methyl-2-buten-3-yne (1.58 g, 24 mmole, obtained according to L. Brandsma, ref. cited, pages 88 and 203) in monoglyme (60 ml, freshly distilled from LiAlH$_4$) was introduced a solution of n-butyllithium in hexane (1.6N, 13.8 ml, 22 mmole), dropwise and at −20°, followed 45 min later by a solution of the aldehyde prepared according to d) (3.80 g, 17.9 mmole) in monoglyme (19 ml). The mixture was allowed to warm to 0° within 60 min and then to room temperature. 30 min later, it was hydrolyzed by adding a saturated aqueous NH$_4$Cl solution. The reaction mixture was then extracted with ether and the organic phase was treated as described before. 4.91 g of crude product (yield: 98.6%), suitably pure for the next step, were obtained.

NMR ($^1$H,360 MHz): 1.82(s,3H); 1.88(s,3H); 3.40, 3.50, 3.83(3m,4H); 4.6(m,2H); 5.1, 5.28(2s,2H); 5.40(t,J=7.6 Hz,1H) δ ppm.

f)
(3E,7Z)-2,7-dimethyl-10-(tetrahydro-2(2H)-pyranyloxy)-1,3,7-decatrien-5-ol To a suspension of LiAlH$_4$ (1.33 g, 35 mmol) in anhydrous THF (135 ml, freshly distilled from LiAlH$_4$) was added dropwise a solution of 4.91 g (35 mmole) of the alcohol prepared according to e) in THF (67 ml). After refluxing for 60 min, the chromatographic analysis showed complete absence of said alcohol in the reaction mixture. The latter was cooled and carefully hydrolyzed with ice, followed by a saturated aqueous NH$_4$Cl solution. Extraction with ether, followed by the usual treatment of the organic phase, yielded 4.90 g (yield: 99.2%) of crude product which was used without purification in the next step.

NMR ($^1$H,360 MHz): 1.78(s,3H); 1.85(s,3H); 3.40, 3.50, 3.78, 3.84(4m,4H); 4.31(m,1H); 4.58(m,1H); 4.97(s,2H); 5.37(m,1H); 5.71(d×d,J$_1$=14.4 Hz, J$_2$=7.2 Hz,1H); 6.36(d,J=14.4 Hz,1H) δ ppm.

g) (3Z,7E)-4,9-dimethyl-3,7,9-decatrien-1,6-diol

A solution of the compound prepared according to f) (4.90 g, 17.5 mmole) in methanol (39 ml) was treated with an aqueous 10% HCl solution (10 ml) for 40 min. After extraction with ether and the usual treatment of the organic phase, 3.60 g of crude diol were obtained and, after purification by MPLC [LOBAR ® column (origin: Merck), 1:1 mixture of hexane-ethyl acetate as elution agent] 2.08 g of semi-crystalline diol were obtained (yield: 60.6%).

IR (liq.): 3300, 1610, 1120, 1060, 980, 890 cm$^{-1}$;
UV(MeOH): 228 nm (ε=16584);

NMR ($^1$H,360 MHz): 1.80(s,3H); 1.85(s,3H); 3.59(d×d×d,J$_1$=J$_2$=10.4 Hz, J$_3$=4.3 Hz,1H); 3.71(d×d×d,J$_1$=10.4 Hz,J$_2$=J$_3$=5.4 Hz,1H); 4.35(m,1H); 4.98(s,2H); 5.35(t,J=8.6 Hz,1H); 5.70(d×d,J$_1$=14.4 Hz,J$_2$=5.8 Hz,1H); 6.34(d,J=14.4 Hz,1H) δ ppm;

MS: 196(0,M+); m/z: 97(100), 67(33), 69(23), 41(19), 79(16), 55(13), 105(5), 127(4), 119(3), 145(2), 178(1).

h)
(E)-2,3,6,7-tetrahydro-4-methyl-2-(3-methyl-1,3-butadienyl)oxepin

To an ice-cool solution of the diol prepared according to g) (2.0 g, 10.2 mmole) in pyridine (22 ml) was added p-toluenesulfonyl chloride (2.13 g, 11.2 mmole) in small portions and over 30 min. The mixture was stirred at 0° for 30 min and then stored overnight at 3°. The usual extraction with ether and treatment of the organic phase gave 2.85 g of a crude product which, on thin layer chromatographic analysis, showed two components. The further purification of this product by MPLC [LOBAR ® column (origin: Merck), mixture of hexane-ethyl acetate as elution agent] gave 2.20 g (yield: 61.6%) of the desired product, i.e. 6-hydroxy-4,9-dimethyl-3,7,9-decatrienyl p-toluenesulfonate, and 220 mg of an unidentified by-product. A suspension of sodium hydride (ca. 80%, 630 mg, ca. 21 mmole; previously washed with anhydrous pentane) in monoglyme (30 ml, freshly distilled from LiAlH$_4$) was prepared under argon and cooled to 0°. 900 μl (7.48 mmole) of DMPU (N,N'-dimethyl-N,N'-propylen urea) were added to the suspension and, afterwards, dropwise, a solution of the abovementioned p-toluenesulfonate (2.20 g, 6.28 mmole) in monoglyme (30 ml). The mixture was allowed to warm to room temperature and was stirred overnight. It was then extracted with ether and the organic phase was washed to neutrality, dried and concentrated as usual. 1.14 g of the crude oxepin were thus obtained. This product was further purified by MPLC [LOBAR ® column (origin: Merck), 95:5 mixture of hexane-ether as elution agent] and then by bulb-to-bulb distillation. 450 mg of pure (E)-2,3,6,7-tetrahydro-4-methyl-2-(3-methyl-1,3-butadienyl) oxepin were obtained.

B.p. 110°–120°/14.63×10$^2$ Pa; yield 40.5%

IR (liq.): 1610, 1160, 1120, 1110, 1050, 970, 890 cm$^{-1}$;
UV(MeOH): 228 nm (ε=24865);

NMR ($^1$H,360 MHz): 1.76(s,3H); 1.84(s,3H); 3.54(d×d×d,J$_1$=J$_2$=12.0 Hz, J$_3$=1.0 Hz,1H); 4.04(m,2H); 4.98(s,2H); 5.60(broad s,1H); 5.69(d×d,J$_1$=16.0 Hz,J$_2$=6.5 Hz,1H); 6.33(d×d,J=16.0 Hz,1H) δ ppm;

MS: 178(2,M+); m/z: 67(100), 82(35), 81(12), 41(9), 53(9), 91(6), 135(4), 110(3), 163(3).

EXAMPLE 2

Preparation of
(E)-4-methyl-2-(3-methyl-1,3-butadienyl)oxepane a) 6,6-dimethyoxy-4-methyl-1-hexanol

A solution of citronellal dimethyl acetal [55.0 g, 275 mmole, prepared from racemic citronellal, according to the process described by V. R. Mamdapur et al. in Tetrahedron 20, 2601 (1964)] in methanol (550 ml) was treated at −75° with a stream of ozone for 3.5 h (4.5 g of O$_3$ per hour, 328 mmole of O$_3$). The excess of ozone was purged with argon, the solution was allowed to warm to 0° and then treated with a solution of NaBH$_4$ (5.22 g, 137.5 mmole) in MeOH-H$_2$O (1:1, 154 ml). After 2 h, the reaction mixture was concentrated at reduced pressure, then extracted with ether, and the organic phase was washed to neutrality, dried over MgSO$_4$ and concentrated at reduced pressure. 60.2 g of the desired hexanol (ca. 85% pure) were thus obtained and this product was used as such in the next preparation step. An analytical sample, obtained by preparative GLC (gas-liquid chromatography) gave the following data:

IR (liq.): 3350, 1200, 1130, 1060 cm$^{-1}$;

NMR ($^1$H,360 MHz): 0.93(d,J=6.1 Hz,3H); 3.31(s,6H); 3.63(t,J=6.1 Hz,2H); 4.67(t,J=6.1 Hz,1H) δ ppm;

MS: 176(0,M+), m/z: 75(100), 85(22), 61(18), 69(17), 41(12), 55(12), 95(8), 113(7), 145(3).

b) 6,6-dimethoxy-4-methylhexyl acetate

The crude alcohol obtained according to a) (60.2 g) was acetylated in acetic anhydride (75 ml) in the presence of pyridine (150 ml), at room temperature and overnight. The extraction with ether and the treatment of the organic phase as previously described, followed by distillation of the crude product on a 12 cm Vigreux column, afforded 49.8 g of the desired acetate (ca. 90% pure; yield: 74.8%; p.b. 120°–125°/14.67×10$^2$ Pa).

An analytical sample obtained by preparative gas chromatography gave the following data:

IR (liq.): 1740, 1250, 1140, 1060 cm$^{-1}$;

NMR ($^1$H,360 MHz): 0.93(d,J=6.5 Hz,3H); 2.05(s,3H); 3.32(s,6H); 4.05(t,J=7.2 Hz, 2H); 4.46(t,J=6.1 Hz,1H) δ ppm;

MS: 216(0,M+), m/z: 75(100), 85(39), 43(16), 95(13), 55(10), 113(4), 126(4), 187(1).

c) 5-formyl-4-methylpentyl acetate

To a solution of the acetate prepared according to b) (47.9 g, ca. 200 mmole) in acetone (880 ml) was added water (13.2 ml) and AMBERLYST® 15 (8.8 g; origin: Rohm & Haas). After stirring for 2 h, GLC-analysis indicated still 30% of residual acetate. A second batch of AMBERLYST® (4.4 g) and water (6.6 ml) was added, followed by a third batch after another 2 h. When conversion of the acetate was complete (5.5 h total) the suspension was filtered and concentrated under reduced pressure. The residue was diluted with dried over MgSO$_4$ and concentrated. The crude product was distilled through a 12 cm Vigreux column to give 31.4 g of the desired aldehyde, about 90% pure (yield: 83%; p.b. 115°–120°/14.67×10$^2$ Pa.)

An analytical sample prepared by GLC gave the following data:

IR (liq.): 1730, 1250, 1050 cm$^{-1}$;

NMR ($^1$H,360 MHz): 0.98(d,J=6.5 Hz,3H); 2.05(s,3H); 4.06(t,J=5.8 Hz,2H); 9.77(t,J=1.0 Hz,1H) δ ppm;

MS: 172(0,M+), m/z: 43(100), 69(88), 68(61), 61(57), 55(28), 56(25), 84(15), 97(15), 129(9).

d) (E)-4,9-dimethyl-7,9-decadien-1,6-diol

The process described in Example 1e) was followed, using 14.4 g (218 mmole) of 3-methyl-3-buten-1-yne in 400 ml of monoglyme, 121 ml of the solution of n-butyllithium in hexane (1.6N, 197 mmole) and 30.96 g of the aldehyde prepared according to c) (ca. 90% pur, 160 mmole) in 150 ml of monoglyme. After extracting with ether and treating the organic phase in the usual way, 47.50 g of a mixture containing 58% of (E)-10-acetoxy-2,7-dimethyl-3-decyn-1-en-5-ol and two other by-products were obtained. This mixture was dissolved in THF (600 ml) without further purification and treated with a suspension of LiAlH$_4$ (11.0 g, 289 mmole) in THF, in a manner identical to that described in Example 1 f). 35.0 g of crude product were obtained and purified on a silica-gel column (250 g, and as eluting agent a mixture of 1:1 hexane/ethyl acetate). 20.5 g of a 93% pure 1:1 mixture of two diastereoisomers of the desired diol were obtained. A further purification of this mixture by gas chromatography did not allow the separation of the two isomers (yield: 57%).

IR (liq.): 3350, 3080, 1620, 980, 900 cm$^{-1}$;

UV(MeOH): 228 nm (ε=21780);

NMR ($^1$H,360 MHz): 0.93, 0.95(2d,J=6.1 Hz,3H); 1.85(s,3H); 3.63(t,J=5.8 Hz,2H); 4.27(d×d×d,J$_1$=J$_2$=J$_3$=6.5 Hz,1H); 4.98(s,2H); 5.62, 5.66(2d×d,J$_1$=15.8 Hz,J$_2$=6.5 Hz,1H); 6.3(d,J=15.8,1H) δ ppm;

MS: 198(0,M+), m/z: 69(100), 55(77), 97(85), 41(50), 83(61), 111(21), 129(20), 165(4), 180(3).

e) (E)-4-methyl-2-(3-methyl-1,3-butadienyl)oxepane

The method described in Example 1 h) was followed, using 10.0 g (ca. 50 mmole) of the diol prepared according to d), 200 ml of pyridine and 10.1 g (53 mmole) of p-toluenesulfonyl chloride. After extraction with ether and the usual treatment of the organic phase, 13.3 g of crude product were obtained and purified by chromatography to afford 8.52 g of 6-hydroxy-4,9-dimethyl-7,9-decadienyl p-toluenesulfonate, as well as 1.65 g of an unidentified by-product.

The procedure described in Example 1 h) was carried on with 2.68 g of NaH (111 mmole) in 130 ml of monoglyme, 3.80 ml of DMPU (31.6 mmole) and 8.52 g (24 mmole) of the above-mentioned p-toluenesulfonate in monoglyme (130 ml). After purification of 5.1 g of crude product, 3.0 g of a more than 98% pure mixture, containing two diastereoisomeric forms (ca. 1:1) of (E)-4-methyl-2-(3-methyl-1,3-butadienyl)oxepane were obtained. P.b. 111°–112°/14.67×10$^2$ Pa; yield: 69%.

The two diastereoisomers were separated by repeated preparative gas chromatography.

Diastereoisomer A

IR (liq.): 3090, 1615, 980, 900 cm$^{-1}$;

UV(MeOH): 228 nm (ε=25527);

NMR ($^1$H,360 MHz): 0.98(d,J=6.8 Hz,3H); 1.84(s,3H); 1.95(m,1H); 3.53(m,1H); 3.85(m,1H); 4.20(d×d×d,J$_1$=J$_2$=J$_3$=6.1 Hz,1H); 4.95(s,2H); 5.68(d×d,J$_1$=15.1 Hz,J$_2$=6.1 Hz,1H); 6.29(d,J=15.1 Hz,1H) δ ppm;

NMR ($^{13}$C,90.5 MHz): 18.6(q); 23.2(q); 29.9(d); 30.6(t); 36.1(t); 43.1(t); 69.5(t); 77.7(d); 116.1(t); 131.9(d); 132.0(d); 141.7(s) δ ppm;

MS: 180(30,M+), m/z: 69(100), 41(100), 165(78), 55(75), 81(61), 96(57), 111(44), 137(17), 121(21).

Diastereoisomer B

IR (liq.): 3090, 1615, 980, 900 cm$^{-1}$;

UV(MeOH): 228 nm (ε=27964);

NMR ($^1$H,360 MHz): 0.97(d,J=6.5 Hz,3H); 1.84(s,3H); 3.78(m,2H); 4.08(d×d×d,J$_1$=10.8 Hz,J$_2$=6.1 Hz,J$_3$=2.1 Hz,1H); 4.95(s,2H); 5.67(d×d,J$_1$=16.2 Hz,J$_2$=6.1 Hz,1H); 6.28(d,J=16.2 Hz,1H) δ ppm;

NMR ($^{13}$C,90.5 MHz): 18.5(q); 23.9(q); 29.0(t); 33.6(d); 35.0(t); 45.4(t); 67.3(t); 78.2(d); 116.1(t); 131.7(d); 131.9(d); 141.7(q) δ ppm;

MS: 180(33,M+), m/z: 69(100), 41(100), 55(82), 165(80), 81(63), 96(60), 111(43), 137(15), 123(12), 151(5).

EXAMPLE 3

Preparation of 2-(3-ethoxy-3-methyl-1-butenyl)-2,3,6,7-tetrahydro-4-methyl-oxepin 50 mg of the oxepin prepared according to Example 1 and 20 mg of p-toluenesulfonic acid in 10 ml of ethanol were warmed up to 50° C. for 3.5 h. The reaction mixture was diluted with water and extracted with ether. A crude product was obtained which contained 10% of the desired oxepin. The latter was separated by preparative gas chromatography.

NMR ($^1$H,360 MHz): 1.16(t,J=7 Hz,3H); 1.28(s,6H); 1.76(s,3H); 2.07(d,J=18 Hz,1H); 2.15(m,1H); 2.39(broad t,1H); 2.54(d×d,J$_1$=18 Hz,J$_2$=11 Hz,1H); 3.35(q,J=7 Hz,2H); 3.53(d×d,J$_1$=J$_2$=11 Hz,1H); 4.01(m,2H); 5.60(m,1H); 5.62(d×d,J$_1$=7 Hz,J$_2$=16 Hz,1H); 5.68(d,J=16 Hz,1H) δ ppm;

MS: 224(M+,0,5), m/z: 209(4), 178(8), 163(4), 155(5), 142(3), 135(5), 113(13), 97(5), 87(11), 82(40), 67(100), 41(27).

EXAMPLE 4

Perfuming Composition of the Floral-Fruity Type

A perfuming composition of the floral-fruity type was prepared by admixture of the following ingredients:

| Ingrédient | Parts by weight |
| --- | --- |
| Citronellol | 2000 |
| Phenylethyl alcohol | 2000 |
| IRALIA ®[1] | 1000 |
| Phenylhexanol | 500 |
| Terpineol | 500 |
| Linalol | 500 |
| 2-Phenylethyl 2-methylbutanoate | 500 |
| Ethyl decanoate | 500 |
| Synthetic muguet | 2000 |
| Total | 9500 |

[1]methylionone; origin: Firmenich SA, Geneva, Switzerland

The addition of 0.5% by weight of (E)-2,3,6,7-tetrahydro-4-methyl-2-(3-methyl-1,3-butadienyl)oxepin or of (E)-4-methyl-2-(3-methyl-1,3-butadienyl)oxepane to this base composition provided a new composition with an enhanced rosy and fruity character, with a lot more volume and strength than the original composition. The odor note developed by this new composition was very much richer and had a pronounced diffusion power.

EXAMPLE 5

Preparation of a Perfumed Soap

To a mass of soap chips obtained from a sodium soap base prepared from coconut oil and tallow were added 0.2% of one of the compounds of the invention cited in the preceding example. As a result, the soapy fatty note was suppressed and the soap thus perfumed developed a rosy-fruity note of remarkable strength and diffusive power.

EXAMPLE 6

Fruity Flavor Composition, Mango Type

A fruity flavoring composition, with a mango type flavor, was prepared by admixing the following ingredients:

| Ingrédient | Parts by weight |
| --- | --- |
| 10%* Buchu oil | 15 |
| Ethyl butylate | 100 |
| Ethyl caproate | 50 |
| γ-Decalactone | 30 |
| Geranyl butyrate | 20 |
| Hexanal | 5 |
| cis-3-Hexenol | 10 |
| Hexyle acetate | 40 |
| Hexyle caproate | 40 |
| 0.1%* α-Ionone | 10 |
| Isobutyl cinnamate | 30 |
| Lemon TETRAROME ®[1] | 25 |
| Orange TETRAROME ®[2] | 20 |
| 95% Ethyl alcohol | 605 |
| Total | 1000 |

*in ethyl alcohol
[1]terpeneless lemon oil; origin: Firmenich SA, Geneva, Switzerland
[2]terpeneless orange oil; origin: Firmenich SA, Geneva, Switzerland The mango type base composition thus obtained was used to prepare three flavor compositions by admixing with the following ingredients:

| Ingrédient | Composition (parts by weight) | | |
| --- | --- | --- | --- |
| | A | B | C |
| Mango base | 100 | 100 | 100 |
| (E)-2,3,6,7-tetrahydro-4-methyl-2-(3-methyl-1,3-butadienyl)oxepin | — | 3 | — |
| (E)-4-methyl-2-(3-methyl-1,3-butadienyl)oxepane | — | — | 2 |
| 95% Ethyl alcohol | 900 | 897 | 898 |
| Total | 1000 | 1000 | 1000 |

The compositions A, B and C were evaluated for comparison by a panel of expert flavorists in an acid sugar syrup (10% sugar, 0.1% citric acid) at 0.1% in spring water.

According to the experts, composition B was more fruity and juicy and had more body than composition A. Furthermore, it had a more natural mango character. As for composition C, it had the woody, floral and rosy character which is typical of Brazilian mango and which was not found in composition A. Therefore, the addition of a compound according to the invention to a mango type base composition resulted in an improved flavor composition, with a more natural mango character. In addition, it was found that each of the compounds of the invention imparted a different mango character to said base composition.

What we claim is:

1. A compound of formula

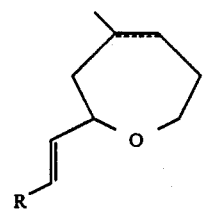

(I)

wherein the dotted line indicates the location of a single or double bond and the symbol R stands for an isopropenyl radical or a 1-ethoxy-1-methylethyl radical.

2. The compound of formula (I) according to claim 1, in its essentially pure form and free from the natural origin substances which are present in the quince fruit, its extracts or fractions derived therefrom.
3. (E)-2,3,6,7-tetrahydro-4-methyl-2-(3-methyl-1,3-butadienyl)oxepin.
4. (E)-4-methyl-2-(3-methyl-1,3-butadienyl)oxepane.
5. A compound according to claim 4, having the formula
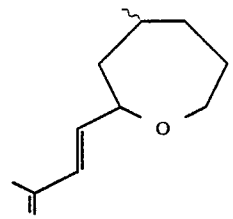 (II)
wherein the wavy line represents a C—C bond of cis or trans configuration.
* * * * *